() United States Patent  
Heaven et al.

(10) Patent No.: US 8,829,442 B2  
(45) Date of Patent: Sep. 9, 2014

(54) NON-CONTACT MEASUREMENT OF THE DOPANT CONTENT OF SEMICONDUCTOR LAYERS

(75) Inventors: E. Michael Heaven, North Vancouver (CA); Gordon Matthew Deans, West Vancouver (CA); Kenneth Cadien, Edmonton (CA); Stephen Warren Blaine, West Vancouver (CA)

(73) Assignee: Aurora Control Technologies Inc., North Vancouver, British Columbia (CA)

( * ) Notice: Subject to any disclaimer, the term of this patent is extended or adjusted under 35 U.S.C. 154(b) by 0 days.

(21) Appl. No.: 13/696,056

(22) PCT Filed: May 3, 2011

(86) PCT No.: PCT/CA2011/000508
§ 371 (c)(1),
(2), (4) Date: Nov. 2, 2012

(87) PCT Pub. No.: WO2011/137512
PCT Pub. Date: Nov. 10, 2011

(65) Prior Publication Data
US 2013/0043393 A1 Feb. 21, 2013

Related U.S. Application Data

(60) Provisional application No. 61/282,989, filed on May 3, 2010.

(51) Int. Cl.
*G01J 5/02* (2006.01)
*H01L 21/66* (2006.01)

(52) U.S. Cl.
CPC ............................... *H01L 22/12* (2013.01)
USPC ....................................... 250/341.4

(58) Field of Classification Search
CPC ........................... H01L 22/12; G01N 21/3563
USPC .............................. 250/341.1–341.8
See application file for complete search history.

(56) References Cited

U.S. PATENT DOCUMENTS

| 3,017,512 A | 1/1962 | Wolbert |
| 4,555,767 A | 11/1985 | Case et al. |
| 5,604,581 A | 2/1997 | Liu et al. |

(Continued)

FOREIGN PATENT DOCUMENTS

WO   WO 2011/137512 A1   11/2011

OTHER PUBLICATIONS

International Search Report dated Aug. 11, 2011, issued by the Canadian Intellectual Property Office in connection with corresponding PCT Application No. PCT/CA2011/000508, filed May 3, 2011.

(Continued)

*Primary Examiner* — Kiho Kim  
(74) *Attorney, Agent, or Firm* — Klarquist Sparkman, LLP

(57) ABSTRACT

A system and method of non-contact measurement of the dopant content of semiconductor material by reflecting infrared (IR) radiation off of the material and splitting the radiation into two beams, passing each beam through pass band filters of differing wavelength ranges, comparing the level of energy passed through each filter and calculating the dopant content by referencing a correlation curve made up of known wafer dopant content for that system.

29 Claims, 9 Drawing Sheets

(56) References Cited

U.S. PATENT DOCUMENTS

| | | | |
|---|---|---|---|
| 5,822,137 A * | 10/1998 | Abul-Haj et al. | 359/808 |
| 5,841,138 A * | 11/1998 | Prekel et al. | 250/341.1 |
| 5,900,633 A | 5/1999 | Solomon et al. | |
| 6,151,119 A * | 11/2000 | Campion et al. | 356/630 |
| 6,242,739 B1 | 6/2001 | Cherkassky | |
| 2004/0061057 A1 * | 4/2004 | Johnson et al. | 250/341.1 |
| 2009/0321647 A1 * | 12/2009 | Shelley et al. | 250/339.07 |
| 2010/0043706 A1 * | 2/2010 | Jung et al. | 118/712 |

OTHER PUBLICATIONS

Wurfel et al., "Diffusion lengths of silicon solar cells from luminescence images," *Journal of Applied Physics*, Jun. 27, 2007, vol. 101, Issue 12, 10 pages.

* cited by examiner

NON-CONTACT MEASUREMENT OF THE DOPANT CONTENT OF SEMICONDUCTOR LAYERS

CROSS REFERENCE TO RELATED APPLICATIONS

This is the U.S. National Stage of International Application No. PCT/CA2011/000508, filed May 3, 2011, which was published in English under PCT Article 21(2), which in turn claims the benefit of U.S. Provisional Application No. 61/282,989, filed May 3, 2010. The provisional application is incorporated herein in its entirety.

FIELD OF THE INVENTION

This invention relates generally to the measurement of the dopant content in one or more layers of a semiconductor device and more specifically to systems and methods of non-contact measurement of the dopant content of such devices in an associated commercial fabrication line, such as for photovoltaic (PV) solar cells, LEDs and any other semiconductor devices employing diffused, implanted or epitaxially deposited doped layers.

BACKGROUND

As background, we will describe both the crystalline silicon (c-Si) PV cell fabrication process and the semiconductor LED fabrication process.

To make a c-Si PV cell, a silicon wafer is subjected to a series of processing steps in a cell fabrication line. Each incoming wafer is lightly bulk-doped (i.e. diffused throughout) with atoms that creates "free carriers" (in semiconductor parlance) of a either positive electrical potential (n-type wafers) or negative electrical potential (p-type wafers). The first step (after incoming inspection to discard defective wafers or to sort the wafers into lots) is to run the wafers through a wet chemical etching process to remove saw marks and other surface defects and contamination. Each wafer is then isotropically textured (another wet process) to microscopically roughen its surface, enhancing its ability to capture incident photons. After texturing, the wafer is then doped with a chemical that creates "free carriers" (in semiconductor parlance), of the opposite electrical potential to the bulk doping, in a layer on the surface(s) of the wafer. In current practice, this doping may occur in one of methods—an "in-line" method or a "batch" method. The in-line method deposits the dopant chemical on the top surface of the wafer, usually carried in a liquid form. (In the case of a phosphorus dopant, this carrier is most commonly phosphoric acid). The deposited dopant carrier is then dried and the resultant product is then diffused (using a high-temperature furnace) into each wafer to form a semiconductor junction that will allow the wafer to produce electricity when exposed to sunlight. In this in-line method the wafers are conveyed continuously through the equipment performing these steps, which typically consist of first a "doper" machine to apply the liquid carrier, then a "dryer" machine to dry the carrier, leaving the dopant chemical on the surface, and a third machine, an in-line diffusion furnace which diffuses the dopant into the wafer. In the batch method, the wafers are loaded into a cassette (most commonly made of quartz and called a "boat" in semiconductor parlance) which is inserted into a "tube" diffusion furnace, which is then sealed, and the wafers are simultaneously exposed to the dopant carrier in gaseous form (most commonly phosphoryl chloride) and heated to diffuse the dopant into the wafers. The wafers are then removed from the furnace, unloaded from the boat and moved to the next part of the fabrication line. In both methods, the amount of dopant introduced, the time spent in the diffusing process and the temperature of the diffusing process determine the penetration depth and concentration by depth of the second dopant. Also, the second dopant is, by nature of the diffusing process introduced and diffused into all of the surfaces of the wafer. Note: from this point onward, "dopant" refers to this second dopant introduced on the surface(s) of the bulk-doped wafer, unless specifically referenced. Each wafer is then wet-etched again to remove phosphosilicate glass (also called PSG, a by-product of the dopant diffusing step) and may be etched to pattern or remove all or a portion of the dopant on the "back" side to prevent shunting. Following this step, a coating (most commonly silicon nitride) is applied to the top surface of the wafer to reduce reflections and passivate the surface. This coating is usually applied using plasma-enhanced chemical vapour deposition equipment. After this, the wafer has metal contacts printed on its top and bottom surfaces, with the top contact pattern designed to minimally interfere with the light exposure to the Si material while providing a path of minimal electrical resistance to the flow of current out of the wafer. These metal contacts (which are printed in the form of a metallic paste) are dried and then diffused into the wafer using a furnace. After this, if the portion of the dopant that is on the back of the wafer has not been previously fully or partially removed, a laser or mechanical device is used to cut a groove around the outside perimeter of the wafer to prevent shunting. Finally, the wafer (which is now a finished PV cell) is tested and graded.

Dopant concentrations, as a function of their distribution within the volume of the wafer, plays a central role in determining the quantum efficiency and other electrical characteristics of the resulting finished PV cell, which ultimately result in its power output capacity and market value. Therefore, the steps within the PV cell fabrication process that are concerned with the quantity and distribution of the dopants that are diffused into the wafer are of paramount importance. Specifically, these steps are: (a) the initial "base" doping of the raw wafer, as supplied by the wafer manufacturer (in most cases at the present time, the raw wafers are positively doped using boron); and (b) the later doping of the outside regions of the wafer (in most cases at the present time this is negative doping using phosphorous). The second doping step forms what is known as the "emitter". We will use the term "base" to refer to the raw wafer doping, and the term "emitter" to refer to the resulting semiconductor formation produced by the second doping step.

In order to ensure that the emitter formation process is within the required specifications, certain measurements are taken that provide an indication of the raw wafer base dopant concentration and the emitter dopant concentration. In current practice, photovoltaic (PV) wafers are often inspected manually or by single-point visual measurement devices that use visible-spectrum industrial cameras at varying intervals in the PV cell fabrication process. Except for the raw material acceptance stage (at the beginning of the fabrication line) and the final inspection and grading (at the end of the fabrication line), continuous in-line measurement of wafers is often limited in scope and coverage, and off-line non-continuous sampling is used instead, particularly for inspection of properties not amenable to interrogation by visible-spectrum industrial camera technology. When off-line sampling is used, in the time interval between samples, hundreds of wafers can pass through the step or steps of interest in the fabrication process. This situation is common at the process steps that determine the application, concentration and distribution of dopants within the PV wafers, and therefore these steps are not well controlled at present, limiting the yield of acceptable finished goods in PV cell manufacturing plants. To raise yields, the industry is now seeking to implement continuous in-line measurements, ideally on 100 percent of the wafers, in order to better control the steps that affect dopant concentration and distribution in the PV wafers.

In addition to the above-described well-established commercial PV cell structure and fabrication process, certain novel PV cell structures and associated fabrication processes are now being introduced to commercial production. These include selective emitter cells, emitter wrap-through cells and interdigitated back contact solar cells (IBC cells). Selective emitter cells vary the emitter dopant concentration to achieve optimal conduction efficiency in the immediate vicinity of the front-side metal contacts (implying heavier doping in these areas) while limited unwanted carrier recombination between the contacts (implying lighter doping in these areas). Emitter wrap-through and IBC cells eliminate shading losses by putting both the emitter and base contacts on the rear of the cell. The invention described herein may be used for measurement of the dopant content of these PV cell geometries as well as the more common front- and back-contact geometry described above.

A semiconductor Light Emitting Diode (henceforth referred to simply as an "LED") performs the opposite function to a PV cell. Instead of absorbing photons to generate electricity, an LED uses electricity to emit photons (a phenomenon called electroluminescence). In LED fabrication the wafers are composed of a neutral substrate such as sapphire. As compared to PV cell fabrication, the wafers are polished rather than textured, each wafer contains multiple LEDs, and the dopants used to create the semiconductor are deposited as epitaxial layers on the surface of the wafer, rather than diffused by the diffusion process used in PV cell manufacturing. Notwithstanding these structural and fabrication differences, these dopant layers may be examined by the same method disclosed in this invention. From this point forward, for simplicity and clarity, PV cell structure will be described without limiting the application of the invention to other doped semiconductor structures.

In PV cell fabrication, a number of existing and novel techniques have been proposed for in-line measurement of emitter doping, but all have serious limitations. For measurement of the diffused dopants, they are Surface Photovoltage (SPV) measurement of diffusion length, eddy current measurement of sheet resistance, and an infrared method for measurement of sheet resistance measurement developed at Germany's Fraunhofer Institute for Solar Energy Research. (J. Isenberg, D. Biro and W. Warta, "Fast, Contactless and Spatially Resolved Measurement of Sheet Resistance by an Infrared Method", Prog. Photovolt: Res. Appl. 2004; 12:539-552). To our knowledge, no method exists for measurement of a wet dopant carrier film.

SPV measurements have been used in the lab for measuring diffusion length (how long an excess carrier in a bulk semiconductor travels, on average, before recombining to achieve equilibrium carrier concentration). See for example: D. K. Schroder, "Surface voltage and surface photovoltage: history, theory and applications", Meas. Sci. Technol. 12 R16-R31, 2001. SPV measurement is typically performed by placing a wafer on a ground electrode (although a non-contact method without a rear sensor plate is possible) and positioning a capacitive probe a small distance above the sample. Because the measurement is capacitive, the measurement area is very limited, the maximum stand-off distance is extremely small and there is little tolerance for wafer bow or vertical movement. Also, in conveyor-fed manufacturing operations, because of the limited stand-off distance there is a significant opportunity for "crashes" causing a jam on the conveyor if any wafers are stuck together (a not uncommon situation), if a wafer breaks and the pieces are not flat on the conveyor (again not uncommon), or if any foreign objects are inadvertently introduced to the conveyor, or if the conveyor itself experiences a small vertical oscillation exceeding the sensor stand-off distance. Finally, because of the requirement for specialized wafer conveyance, and the very close standoff distance requirement for SPV measurement, introduction of such technology into an existing fabrication line may require significant line modifications that can render its usage costly and impractical.

Eddy current measurement has many of the same limitations as SPV and has previously been shown to be unsuitable for in-line measurement of emitter doping (using sheet resistance measurement as the metric). (Rueland, E.; Fath, P.; Pavelka, T.; Pap, A.; Peter, K.; Mizsei, J, "Comparative study on emitter sheet resistivity measurements for inline quality control", Photovoltaic Energy Conversion, 2003. Proceedings of 3rd World Conference on Volume 2, Issue, 12-16 May 2003 Page(s): 1085-1087 Vol. 2.)

The Fraunhofer method, while suitable for the laboratory, has many requirements that make it unsuitable for practical in-line use, most notably the stringent requirement for absence of spurious heat or light that is extremely difficult and expensive to provide in an in-line fabrication environment.

In summary, while it is critical that a commercially viable technique be developed to allow in-line measurement of the electrical properties of PV wafers as determined by the dopant content, no known technique currently exists that is configurable enough to be used in various points in a fabrication line, industrially robust enough to operate reliably, and sufficiently cost effective.

There is consequently a need for a method and apparatus that is flexible, configurable, robust and cost-effective for the purpose of in-line measurement of raw wafer dopant concentration, of the amount and distribution of a wet dopant film emerging from an in-line doper, and of the dopant concentration in an emitter at any step in the manufacturing line following diffusion.

There is further a need for defining specific, repeatable sample sites for each wafer in order to be able to map selective emitter, wrap-through contact and IBC cell doping structures as well as traditional uniform doping. As a corollary, there is also a need for an apparatus and method with the ability to vary the scanning "intensity" (the number of samples taken per unit length in the cross-machine direction over a certain time period), in order to allow the operator to perform periodic or unscheduled in-depth measurement, if necessary.

DETAILED DESCRIPTION

Figure 1:
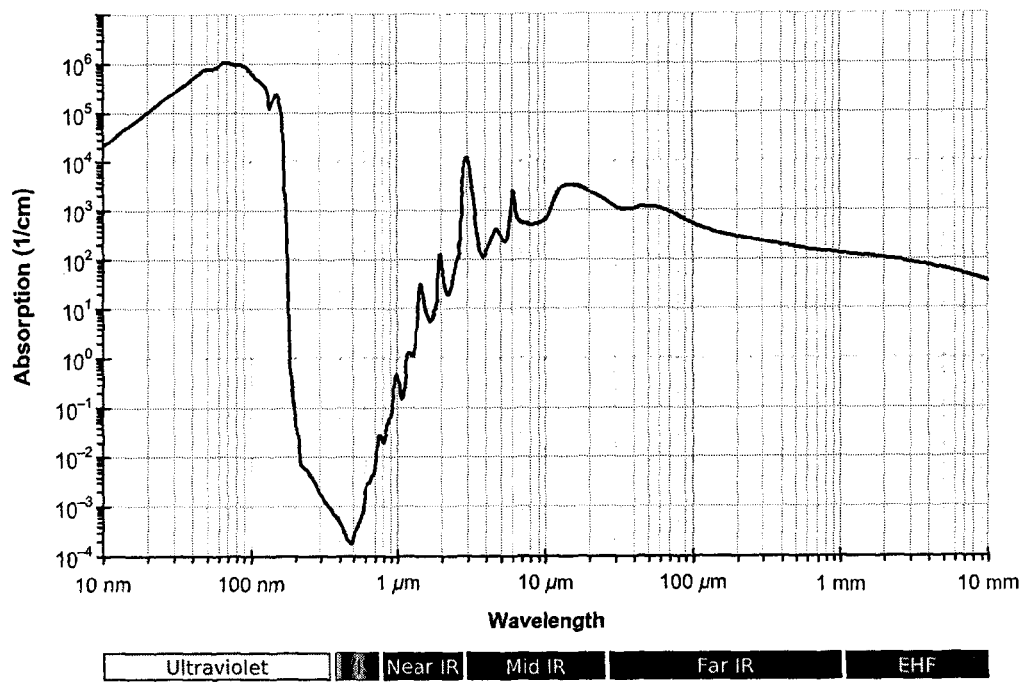
FIG. 1 is a water absorption spectrum graph.

A wet film on a wafer (or any substrate) has electromagnetic absorption and reflection characteristics. In particular, water molecules in a water-based film have characteristic absorption peaks in the infrared ("IR") wavelengths. This is illustrated in the water absorption spectrum graph of FIG. 1. A doped silicon (or indeed any semiconductor) wafer also has a characteristic absorption, reflection amplitude and reflection phase/polarization of infrared radiation corresponding to the spatial concentration of free charge carriers due to the doping. In particular, n-doped silicon exhibits significantly different free carrier absorptions (or as a corollary, reflectance) of infrared spectra at different doping levels, as shown in FIG. 2 and FIG. 3.

Figure 2:
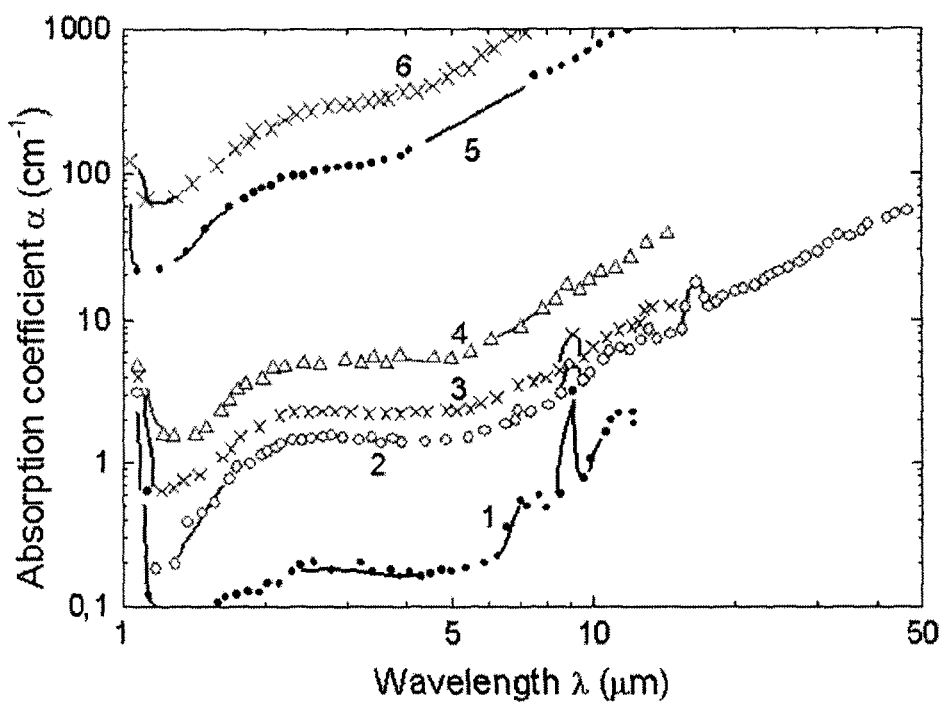
FIG. 2 is a graph of free carrier absorption vs. wavelength at different doping levels (n-Si)

FIG. 2 is a graph of free carrier absorption vs. wavelength for varying negative dopants diffused at different concentrations, forming a negatively doped silicon substrate (n-Si) at 300° K. With reference to the numbers on the graphs of FIG. 2, the dopant concentrations (in atoms per cubic centimeter) are: $1$-$1.4\times10^{16}$ cm$^{-3}$ (arsenic dopant); $2$-$8\times10^{16}$ cm$^{-3}$ (antimony); $3$-$1.7\times10^{17}$ cm$^{-3}$ (antimony); $4$-$3.2\times10^{17}$ cm$^{-3}$ (phosphorus); $5$-$6.1\times10^{18}$ cm$^{-3}$ (arsenic tim alloy); and $6$-$1\times10^{19}$ cm$^{-3}$ (arsenic).

Figure 3:
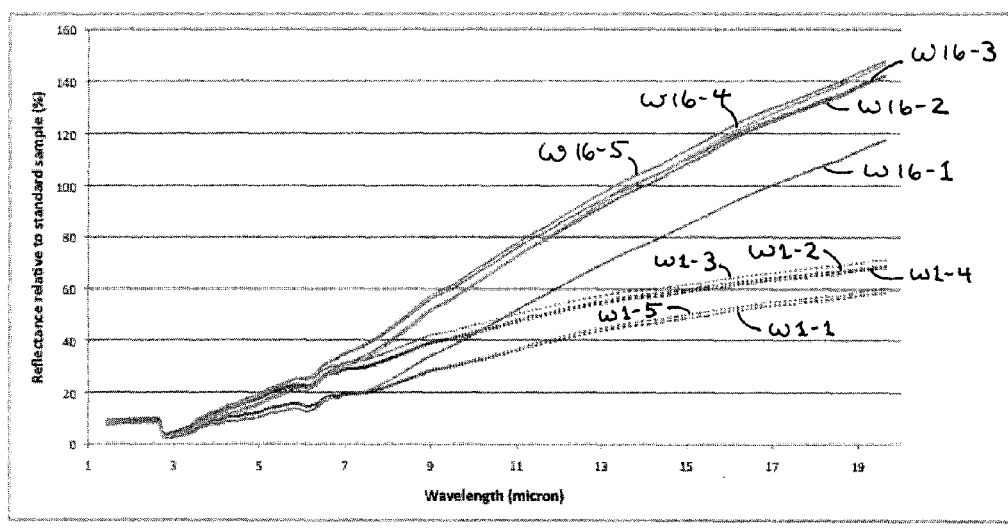
FIG. 3 is a graph of differentiated reflectance of undoped (W1) and doped (W16) c-Si wafers.

FIG. 3 is a graph of differentiated reflectance by infrared wavelength of a two poly-crystalline (poly c-Si) wafers—one bulk-doped with boron only (W1) and another with also a phosphorus layer diffused into its top surface (W16). The numerals 1-5 following W1 and W16 identify segments on each wafer that were examined. The measurements on the graph are normalized with respect to a pure crystalline silicon reference sample. The graph demonstrates that as the incident infrared wavelength lengthens, the corresponding reflectance of the wafer with the phosphorus-doped layer, as compared to the reference sample, is distinctively stronger compared to the bulk-doped wafers, therefore indicating that the added dopant layer is influencing the reflectance as a function of infrared wavelength and as a corollary, the normalized slope of the infrared reflectance versus wavelength can be used to determine the doping level of this layer.

Additionally, the presence of any chemical layer or film, not just phosphorus, and whether diffused or not, upon a dissimilar substrate causes refractions, reflections, wavelength shifts and phase changes that can be used to determine the layer/film thickness and/or conditions at the boundary. The magnitude, phase, polarization and wavelengths of such absorption and reflections are dependent upon the particular films or dopant(s) used, the density and thickness of the film or doping, and the nature of any underlying substrate.

By transmitting infrared radiation at known wavelengths and intensity levels on a wafer or substrate, the absorption of the characteristic wavelengths can be measured as a function of the reflected values observed at the receiver. Phase shifts, wavelength changes, and polarization changes may also be measured. Since the amount of energy absorbed varies in proportion to the amount and composition of the wet film, or to the emitter doping concentration, as the case may be, the wet film concentration, depth and distribution, or the emitter density, respectively, can be measured by measuring the difference between irradiated and reflected energy.

It is desirable to take measurements or samples from multiple, specific locations on the wafer or substrate. This is both because single samples can exhibit wide variance and it may be necessary to smooth these variances, and also because the wafer or substrate may have purposely-differentiated deposition of a wet film or diffusion of a dopant.

Also, for each sample, by using simultaneous differential interrogation at the sample site, the apparatus and method described herein can tolerate light, heat and vibrations from the factory environment and compensate for temperature, varying standoff distances and varying angles of incidence.

Figure 4:
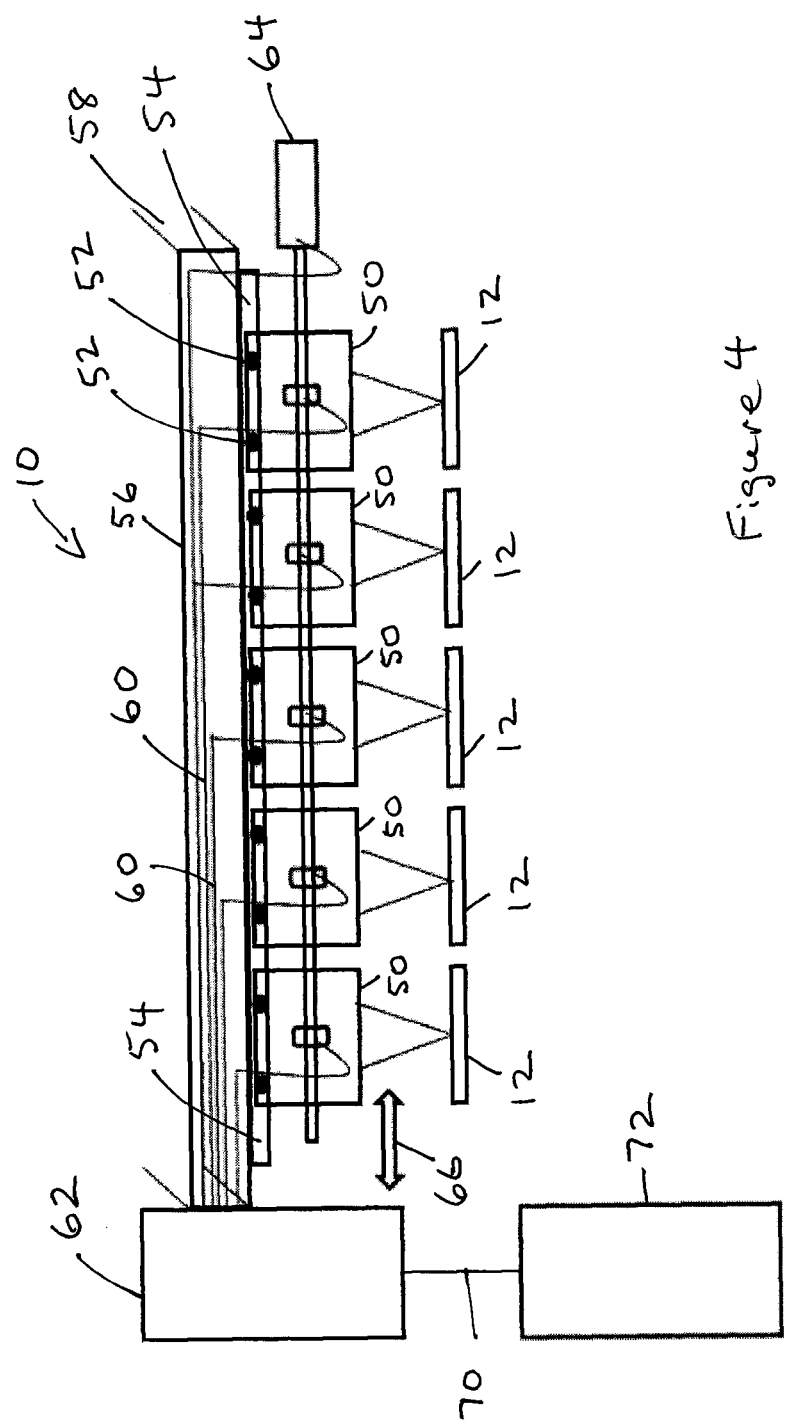
FIG. 4 is a schematic block diagram of a non-contact system for measuring the dopant content of semiconductor material in accordance with an embodiment of the disclosure.

The apparatus 10 described in FIG. 4 is for a multi-lane, conveyor-fed, photovoltaic ("PV") cell fabrication facility. Although it should be understood that single-lane and/or non-conveyor configurations are also possible for LED and other semiconductor fabrication facilities.

One or more transmitters and receivers are mounted over the area where the PV wafer 12 is to be measured. Each receiver consists of two or more sensors—the purpose being to capture differential signal data as explained above. For simplicity and clarity, a non-contact system for measuring the dopant content of doped silicon will be described in respect of an apparatus 14 consisting of a single transmitter 16 and a single receiver 18, the latter consisting of two sensors 20, 22. This is illustrated with reference to FIG. 5, which depicts schematically an alternate embodiment of the disclosure as a block diagram.

A sensor housing containing the equipment in the block diagram is located approximately 50-150 millimeters above the wafer 12 surface.

There are at least three possible embodiments of the transmitter, each containing a different source of infrared radiation. In the first embodiment the source is composed of one or more continuous broadband infrared source(s) mounted in an elliptical reflector. In the second embodiment, the source is composed of a multi-wavelength infrared laser. In the third embodiment the source is composed of two single-wavelength infrared lasers.

Referring to the first embodiment of the transmitter, the elliptical reflector 24 of the infrared source 16 focuses the wide spectrum of infrared radiation from the infrared source to a single point in space. A chopper wheel 26 is located at the focal point of the ellipse which modulates the infrared radiation at approximately 1 kHz, although the radiation may be modulated by any appropriate method, or combination of methods, including amplitude, frequency, pulse, or phase shift modulation. The use of modulation is necessary as the detectors respond to changes in detected signals and because the modulation differentiates the transmitted infrared signal from background infrared radiation and enhances the signal to noise ratio. The modulation can also be used to generate information about the dopant content by measuring its effect on the modulation via the changes induced in the reflected signals.

An off axis elliptical reflector 28 is shown facing the infrared source 16 to receive the modulated radiation. The elliptical reflector 28 focuses the modulated radiation from the chopper wheel 26 onto a measurement point 30 on the wafer 12 at an incidence of approximately 45 degrees to the wafer 12 and aligns the peak of the radiation in the center of the first lens 32 of the receiver 18 (discussed below). Although it will be appreciated that the reflector 28 is not necessary in the second and third embodiments of the transmitter 16 as the lasers are already in collinear format.

There are at least two possible embodiments of each receiver 18. In the first embodiment of the receiver 18, the receiver 18 is mounted above the measurement point 30 where the infrared radiation strikes the wafer 12. The reflected infrared radiation is diffuse and is collected by the first lens 32 and directed to a first narrow band-pass filter 34. The first filter passes a narrow band of infrared radiation centered at a selected wavelength of the infrared spectrum. This wavelength is selected such that effects of the isotropic texturing on the received signal properties of interest are not significant. The other portion of the received radiation is reflected by the first filter 34.

The reflected radiation is directed onto a second narrow band-pass filter 36 centered at a different selected wavelength such that the wavelengths of the two bands do not overlap. Similarly this second wavelength is selected such that any effect of the isotropic texturing on the received signal properties of interest are not significant. In a preferred embodiment, one band pass filter 34 or 36 has the central band-pass at approximately 8 micrometers with a pass-band of +/−125 nanometers and the other filter 34 or 36 has the central band-pass at approximately 10.5 micrometers with a pass-band of +/−175 nanometers.

The radiation that passes the first filter 34 is focused by a second lens 38 onto a first infrared detector or sensor 20 which produces a low voltage signal in proportion to the intensity of the infrared radiation that reaches the first detector 20. The radiation that passes the second filter 36 is focussed by a third lens 40 onto a second infrared detector or sensor 22 which produces a low voltage signal in proportion to the intensity of the infrared radiation that reaches the second detector 22.

The low voltage signal of each detector 20, 22 is amplified by respective amplifiers 42, 44 and then acquired by an analog-to-digital data acquisition board 46 synchronized to the chopper frequency in the transmitter 16 and controlled by a computer 48. Thus the sensors 20, 22 produce two voltage values, proportional to the infrared energy in two narrow bands passing respective first and second filters 34, 36.

The computer 48 uses the voltage from each detector 20, 22 to calculate the slope and/or the ratio between the amount of energy received in each band which, as has been shown above, is proportional to the energy absorbed by the dopant in the top layer of the wafer 12. The dopant content is determined by computation or table look-up based on models of infrared reflections of the wafer material at varying dopant content, in particular (but not limited to) passing the slopes though a correlation curve, as exemplified in FIG. 10.

In a second embodiment of the receiver, a beam splitter is used to split the reflected IR energy at the focal point of the first lens into equal parts and direct the resultant equal parts onto an array of detectors, each with a different band-pass filter in front of the detector. Each detector delivers a voltage in proportion to the intensity of infrared radiation reaching each detector. Thus, multiple points on the doping to wavelength correlation curve are measured, improving the accuracy of the slope measurement (because the slope can vary by wavelength) and therefore the dopant content in or on the semiconductor material.

In a further embodiment of apparatus 14 instead of band pass filter 34 positioned behind lens 32 a beam splitter is positioned behind lens 32. This separates the beam from lens 32 into two beams which are directed to respective band pass filters 34, 36, respective lenses 38, 40 and then respective sensors 20, 22.

Figure 5:
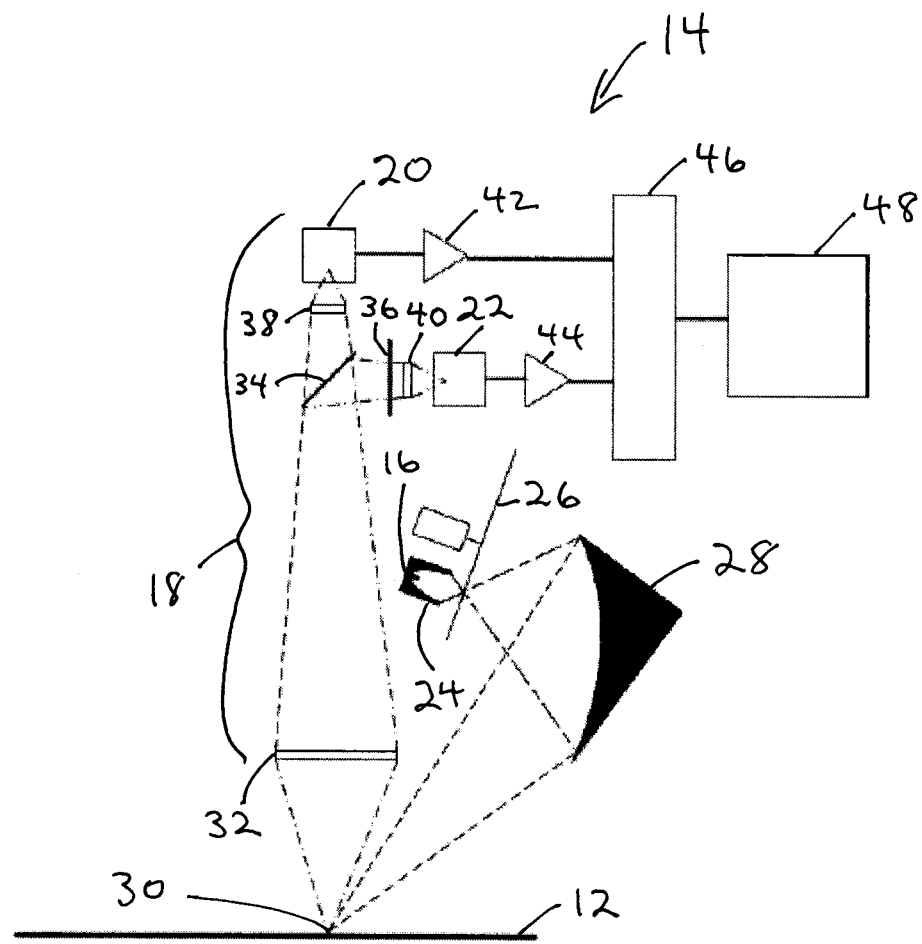
FIG. 5 is a schematic block diagram of a non-contact system for measuring the dopant content of semiconductor material in accordance with an alternate embodiment of the disclosure consisting of a single transmitter and a single receiver, the latter consisting of two sensors.

The subject surface, shown in FIG. 5 as a single semiconductor wafer 12, can also be multiple semiconductor wafers on a conveyor, stationary wafers, or a monolithic surface such as a thin film on a substrate. The surface(s) can be of any size.

A preferred embodiment of a non-contact system for measuring the dopant content of semiconductor material 10 is shown in FIG. 4 in the form of a schematic block diagram. A plurality of sensor heads 50 are mounted between 5 millimeters and 250 millimeters above a wafer conveyor (not shown) in alignment perpendicular to the direction of travel of the conveyor. Each sensor head 50 includes a housing into which the components of the apparatus of FIG. 5 are contained, including a single transmitter 16 and single receiver 18 (from FIG. 5). The receiver 18 incorporates the two sensors 20, 22 (FIG. 5). Furthermore those components are configured to operate in the manner discussed above with reference to FIG. 5. In particular, inside each sensor head is the infrared source 16, chopper wheel 26, focusing reflector 28, lens 32 to collect reflected infrared radiation and to direct the infrared radiation onto a band pass filter 34 or beam splitter, two detectors 20, 22 that produce a voltage in proportion to the amount of infrared radiation in a given frequency range and a means of amplifying 42, 44 and converting 46 this voltage into a digital signal at a frequency synchronized with gaps in the chopper wheel 26.

Each sensor head 50 rides on wheels 52 in a precise track 54 perpendicular to the direction of travel of the conveyor. The track 54 is supported by the support beam 56 which is fixed to the equipment frame 58 or alternatively, supported from the floor. Power to each sensor head is delivered by corresponding power cables 60 from the power and terminations cabinet 62. The power cables 60 are configured so that the heads 50 are free to move along the track 54 over a defined measurement range. The array of sensor heads 50 is moved along the track 54 together in the directions of arrow 66 by a linear actuator 64 which positions each head 50 over a corresponding wafer 12 below, riding on the conveyor. The combination of conveyor and linear actuator 64 movement allows a pattern to be measured across the wafers.

Figure 6:
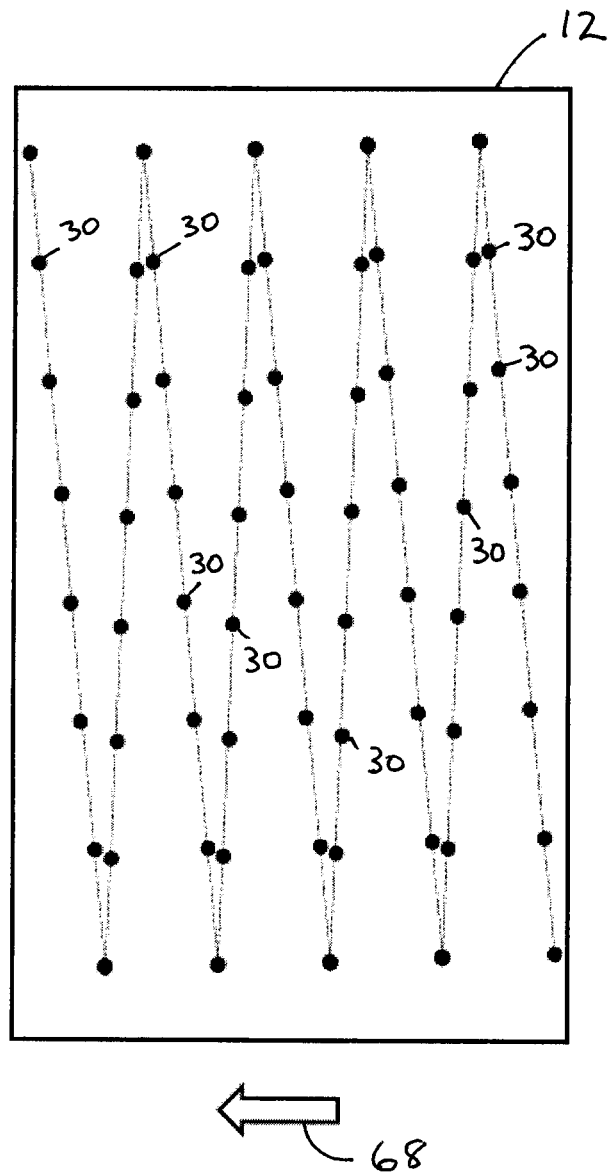
FIG. 6 is a schematic top view of methods of sampling at various test locations of a wafer and sampling patterns in accordance with an embodiment of the disclosure.

When in use, the linear actuator 64 and conveyor move in directions at right angles to each other. This causes the pattern of measurement points 30 to be diagonal in nature, as depicted in FIG. 6. The conveyor moves in the direction of arrow 68. However, if the actuator 64 is moved much faster than the conveyor, it is possible to measure each wafer 12 at several points across the wafer 12. This is exemplified by the pattern of measurement points 30 shown by dots in FIG. 6 some of which are as marked with reference numeral 30. It can be seen from FIG. 6 that when the linear actuator 64 moves in the reverse direction a further diagonal pattern of measurement points 30 can be made. This can be repeated multiple times as the wafer 12 is moved by the conveyor in the direction of arrow 68. The array of measurement points 30 and their location across the wafer 12 for a constant conveyor speed is a function of the sampling rate and the speed of the linear actuator 64.

At each measurement point 30, the amplified voltage from the two detectors 20, 22 of the receiver 18 of each sensor head 50 is converted to a digital signal using a multiplexed analog to digital conversion board 48 and embedded computer 48 located in the sensor head 50 (FIG. 5). The resulting values are sent over a fieldbus or LAN cable that can be combined with power cable 60 to the power and termination cabinet 62. The resultant two measurements at each measurement point 30, as well as the position of the measurement point corresponding to the linear actuator 64 position are sent to a computer 72 and stored for each measurement point 30. The presence of the wafer 12 on the conveyor is known based on a step increase in the overall signal level at the sensors 20, 22.

The sample sites and/or sampling rate on a particular wafer 12 or other substrate may be defined to follow a specific pattern. Additionally, a pattern may be pre-defined, and more than one pattern may be pre-defined. Over a series of samples, one or more patterns may be used, or the sample sites (measurement points 30) and sampling rate may be arbitrarily varied. This variable sampling technique is illustrated in FIG. 6. Additionally, the sample sites may be varied in the "direction of travel" by exploiting the movement of the wafers 12 or other substrate on the conveyor.

In order to make the sampling site locations repeatable from wafer 12 to wafer 12, the sites must be offset from a specific two-dimensional location defined on the subject surface. Where the subject surface consists of multiple wafers 12, two edges of each wafer 12 are used as the reference for all the sampling sites on that wafer 12. These edges are located by detecting the radiation level change in the received signal when a wafer 12 is present versus the signal when only the conveyor is present.

Figure 10:
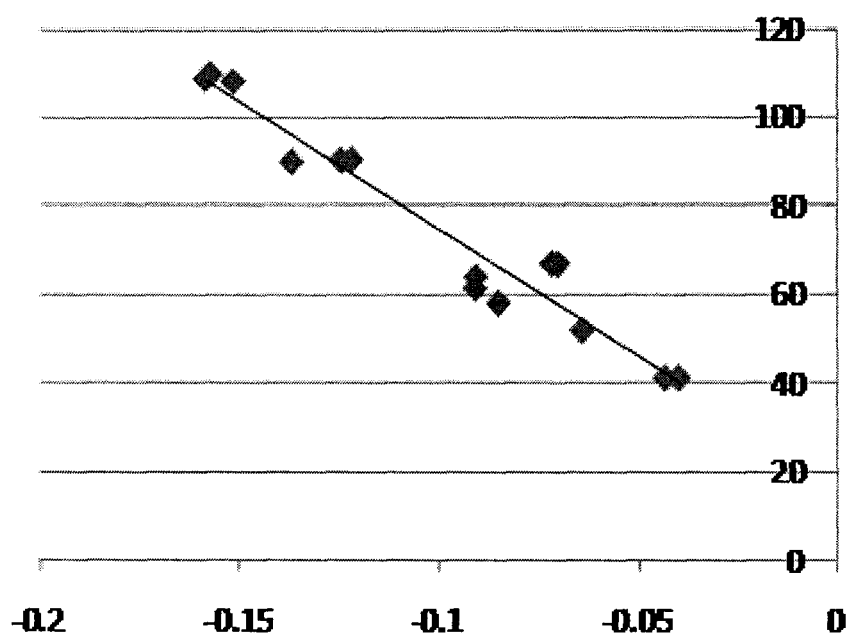
FIG. 10 is a graph of an exemplary diagram showing the correlation of a non-contact system for measuring the dopant content of a layer of semiconductor material to the sheet resistance, as measured by a four-point probe, of said layer of semiconductor material in accordance with embodiments of the disclosure.

The ratio or differences in voltage from each sensor 20, 22 of the receiver 18 in a sensor head 50 is used as the dependent variable in a correlation curve relating this ratio/difference to the independent variable which is the dopant content of the wafer. The correlation curve is determined by passing wafers of known dopant content (measured using a lab-based contacting four point probe or other off-line measurement techniques such as electrochemical capacitance-voltage profiling) under the sensor head 50 and measuring the resulting signals at both sensors 20, 22 and performing a least-squares regression relating the observed ratio/difference in voltage to the known the dopant content from the lab measurement. A correlation curve of the type shown in FIG. 10 is thereby produced and stored in the memory of the computer for reference.

If the wafers 12 are staggered or it is desirable to measure a different pattern on each wafer 12, an alternate embodiment comprises a linear actuator for each sensor head 50 and each head 50 on an independent track. However there is an increase in size of the overall measurement system in the direction of travel of the wafers 12 on the conveyor, in this embodiment.

Figure 7:
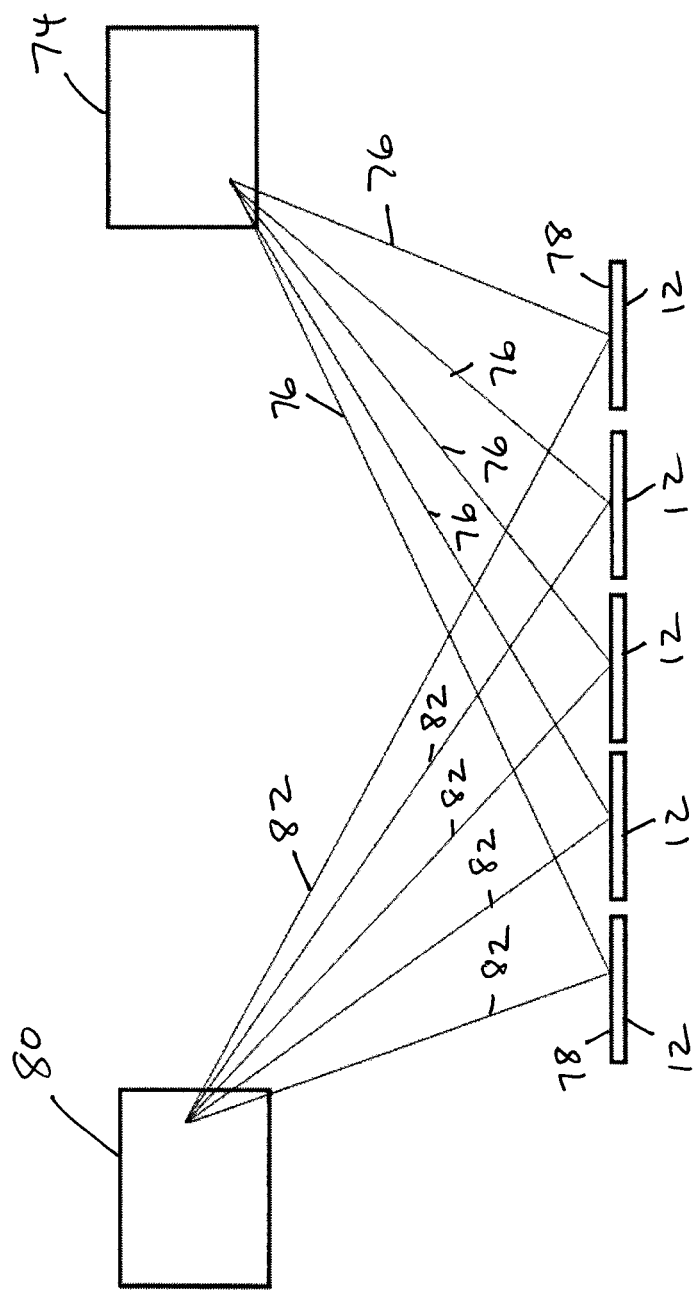
FIG. 7 is a block diagram of a non-contact system for measuring the dopant content of semiconductor material in accordance with an alternate embodiment of the disclosure.

An alternate embodiment of a non-contact system for measuring the dopant content of semiconductor material is shown schematically in FIG. 7. A single transmitter 74 housing a single infrared source of radiation (for example, transmitter or source 16 of FIG. 5) is located on one side of the conveyor (not shown) which holds and transports the wafers 12 as part of a fabrication line such as a PV cell fabrication line. The source can be a broadband source with a focusing lens or a laser with selectable wavelengths. The source can be a continuous broadband infrared source. The focused beam is modulated by a chopping wheel or by electronically modulating the laser onto a steering reflector that directs and focuses the beam of radiation onto a selected point on a wafer. All as previously discussed with reference to FIG. 5.

In this embodiment a steering reflector is rotatable about an axis to change the incidence of the transmitted signal 76 to a selected position on the wafer 12 surface 78 at selected intervals in order to direct and focus the beam in series on a group of wafers in a row. While FIG. 7 depicts several transmitted signals 76 and corresponding several received signals 82, it should be understood that the system operates serially and the signals are not generated, nor are they received, concurrently. Similarly if a laser is employed as the source, the steering reflector rotates about an axis to move the beam to contact selected points on the group of wafers 12 moving on the conveyor.

A receiver 80 is positioned on the other side of the conveyor, with a focusing element and a reflector that is adjusted to see the same point on the wafer that is illuminated by the source beam 76. The resulting beam of radiation 82 is directed on by the focusing element on a detector At the time that the transmitter 74 and receiver 80 are oriented to a particular sample site, the transmitter transmits a beam of radiation 76, and the receiver receives such signal 82 as reflected from the wafer surface 78. This transmission and reception occurs over a specific time period, known as the "sample period". (The number of samples taken over a defined time period is known as the "sampling rate"). The shape and size of the observed portion of the wafer 12 surface 78 at the sample site is the "sample area". Within a sample area, there may be a sub-area defined by the shape and size of a particular area that can be seen by the receiver at any time. This is called a sample "spot".

If the source is a broadband source containing a broad spectrum of infrared energy such as a broadband infrared source, it is necessary to split the received signal into two equal parts using a beam splitter as a part of receiver 80 then focus each half on to two narrow-band pass filters, each with a different center wavelength, within receiver 80. The energy that passes each narrow band-pass filter is focused on a corresponding one of two detectors, converted to a voltage, amplified and converted to a digital signal corresponding to the energy in each band. The slope or ratio between the two measurements is calculated and stored for the given position of the signal defined by the position of the steering reflector position. This is undertaken in the same manner as discussed above with reference to FIG. 5. The source beam is then moved to a new spot on the wafer and the receiver positioned to see the same spot and the process is repeated for the next location.

If the source is a laser with a selectable wavelength, the laser is alternated between two or more wavelengths and focused on a point using the steerable reflector. The receiver consists of a focusing element and reflector focuses the received energy on a single detector whose voltage is amplified and sampled at the frequency corresponding to the laser modulation frequency.

Figure 8:
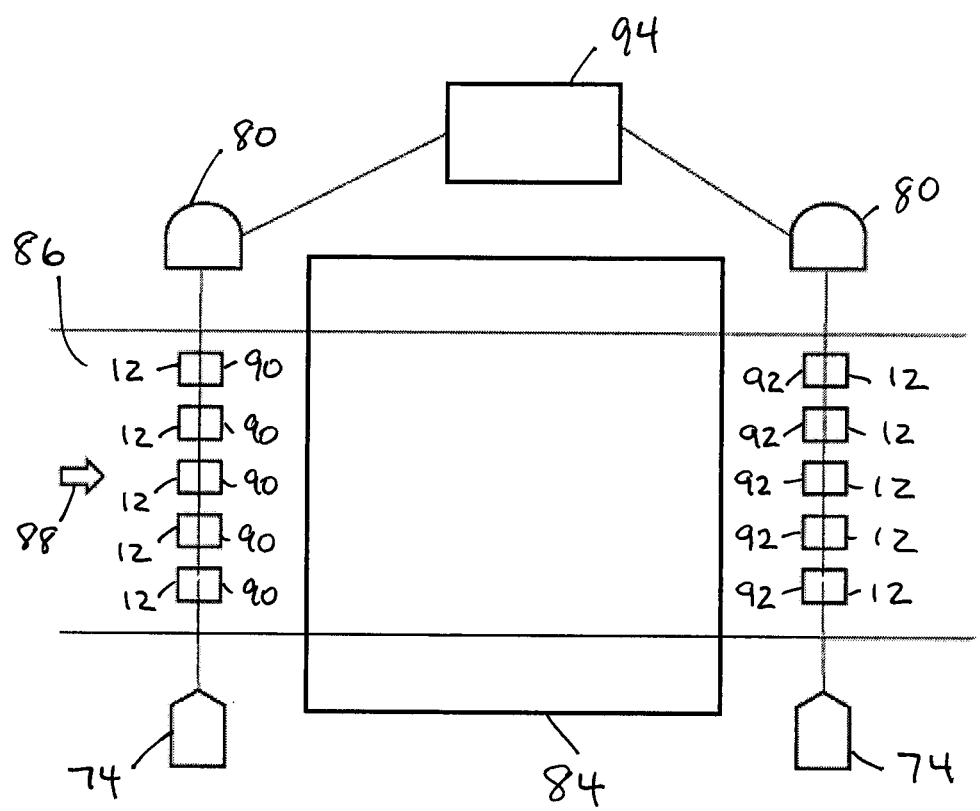
FIG. 8 is a block diagram of a non-contact system for measuring the dopant content of semiconductor material in accordance with an alternate embodiment of the disclosure in which a pair of systems as depicted in FIG. 7 are used on either side of a doping chamber.

An alternate embodiment of a non-contact measurement system for measuring dopant content is shown schematically in FIG. 8 for measuring one or more wafers at the beginning of a process step, or a contiguous series of process steps, then measuring the wafer(s) at the end of the process step(s) and calculating the change in infrared reflectance of the wafer(s). This change is used to determine the exact impact of the process on each wafer.

This embodiment may be used in a semiconductor fabrication process wherever dopant or a dopant carrier (such as phosphoric acid) is applied to a wafer surface, dried, or diffused into a wafer, implanted into a wafer, deposited as one or more epitaxial layers, or etched from the surface of a wafer. It may also be used wherever a wafer is treated to create a surface texture.

In this configuration, the wafers 12 ride on conveyor 86 in the direction of arrow 88. The wafers are measured by the system described with reference to FIG. 7 (with numerical references the same in this FIG. 8) before and after the process, or series of processes, carried out by the machine or sequential set of machines (shown as a single entity) 84. This configuration measures the reflectance of the base wafer 90 before the process(es) and then the reflectance of the wafer 92 after the process(es). Computer 94 controls the measurement and comparison process. The system described with reference to FIG. 4 may be used in this system instead of the system described with reference to FIG. 7.

Without limiting the generality of the foregoing, examples of the use of this embodiment for certain PV cell fabrication steps are now described. In the first example, the machine (84) is a doper machine only, and the embodiment is used for measuring the deposited wet dopant carrier on the wafer(s). In the second example, the machine (84) is an in-line diffusion furnace only, and the embodiment is used for measuring the furnace's effect of diffusing into the wafer(s) the dried dopant that was on the surface of the wafer(s). In the third example, the machine (84) is a diffusion furnace followed by a PSG etch machine, and the embodiment is used for measuring the dopant diffusing and etching process in combination.

Figure 9:
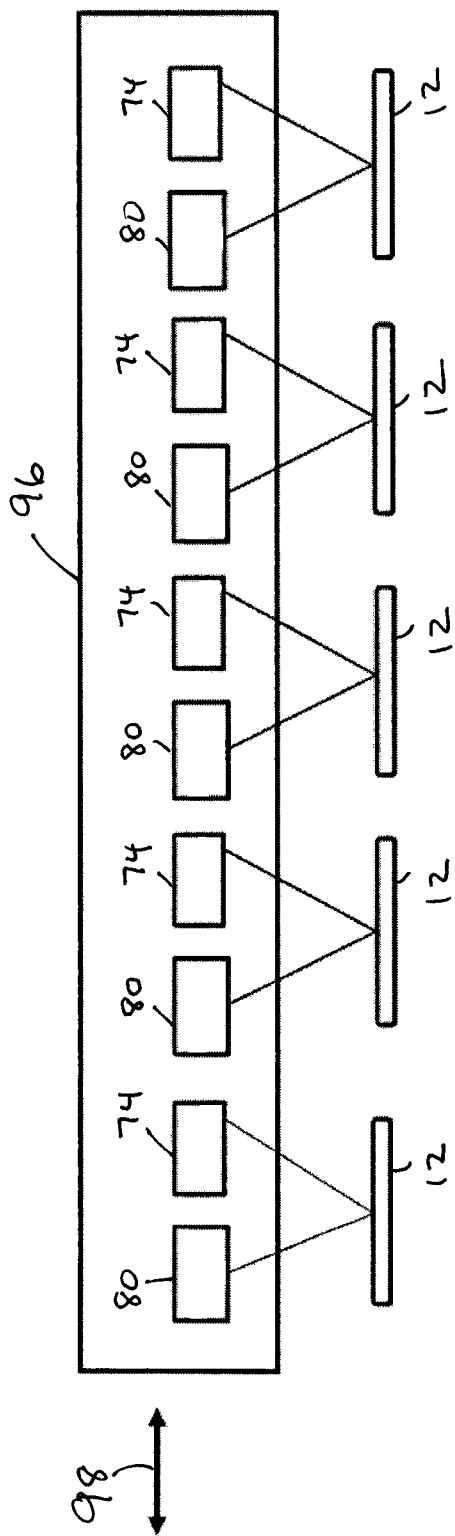
FIG. 9 is a block diagram of a non-contact system for measuring the dopant content of semiconductor material in accordance with an alternate embodiment of the disclosure in which multiple transmitters and receivers are positioned above a series of wafers of semiconductor material.

An alternate embodiment of a non-contact system for measuring the dopant content of semiconductor material is shown schematically in FIG. 9. In this alternate embodiment to the one described with reference to FIG. 4, all the transmitters 74 and receivers 80 (as in FIG. 7) are located in a single supporting structure 96 and the supporting structure 96 is moved together back and forth in the directions of arrow 98 to interrogate the wafers 12 over a pattern as exemplified in FIG. 6.

An example of applicant's method of comparing samples at sensors 20 and 22 is to calculate the difference in the amplitude of the signals received at sensors 20 and 22, divided by the difference between the centre of each of the passbands of the band pass filters 34 and 36, associated with corresponding sensors 20 and 22. On a graph of the reflectance as a function of wavelength, this is the slope of the line intersecting the centre of the passbands of the band pass filters 34 and 36, associated with corresponding sensors 20 and 22. For further clarity, for example, the centre of the passband of band pass filter 34 associated with sensor 20 may be at 8 micrometers, and the centre of the passband of band pass filter 36 associated with sensor 22 might be at 10 micrometers. If the received signal amplitude at sensor 20 is "x" and the received signal value at sensor 22 is "y", then the slope is (y−x)/4. Different slopes represent different amounts of the dopant being detected, and by using the slope, the effect of amplitude variations due to the factors described herein are mitigated.

Similar mitigation can be achieved by using the ratio of the signal amplitudes measured at sensors 20 and 22. In this case, the ratio is defined as y/x. Likewise, either the difference between, or ratio of, the received signal phases or received signal polarization at sensors 20 and 22 can be used.

FIG. 10 is a graph of an exemplary correlation curve of a non-contact system for measuring the dopant content of semiconductor material in accordance with embodiments of the disclosure. In this example, dopant content is represented as sheet resistance. The curve (in this case a line) of the graph is a correlation between off-line four point probe measurements of sheet resistance (y-axis) and the measurements of the slope of the line between two voltage readings from the two detectors (x-axis). It is generated by placing a series of known and increasingly doped wafers on the conveyor and measuring the resulting voltages from each sensor 20, 22, calculating the resulting slope of the line between the two points (or the ratio of the two voltages) and fitting a linear model using least-squares regression. The observed data points are shown with diamond markings and the best-fit with the line. The $R^2$ value represents the degree to which the calculated line fits the observed measurements and the closer the value is to 1.0, the better the fit of the line to the observed data. In the example of FIG. 10 the $R^2$ value is 0.9486. The line is used to calculate the sheet resistance y corresponding to the observed slope x. For example with reference to FIG. 10: y=−575.65x+17.391.

If the slope is −0.1, the sheet resistance is: y=−575.65 (0.1)+17.391=74.9 ohms per square.

A number of samples are taken over a sample area on a wafer or substrate. The values of these samples are collectively processed (for example, but not exclusively, computation of the average value) to provide a meaningful measurement. Each sample area can be well defined and the individual samples do not need to be repeated in exactly the same locations from wafer to wafer or substrate to substrate in order to obtain statistically valid and comparable measurements from wafer to wafer or substrate to substrate.

The pass bands of filters 34 and 36 are chosen to be unequally sensitive to the reflected signal amplitude. By using the comparison between two different values rather than a single absolute measurement, the measurements are normalized to eliminate variations due to any one or more of the following:

Sample-to-sample changes in incident and reflected path lengths and sample area due to scanning across multiple sample sites Sample-to-sample variations in path length, attenuation, or sample area due to vibration or three dimensional position changes in the subject surface (e.g. "bumping" due to conveyor belt irregularities)

Sample-to-sample changes in signal properties due to variations in subject surface texture, crystal boundaries or other surface artifacts such as oxides, phospho-silicate glass, anti-reflective coatings, or contaminants Varying reflectivity due to subject surface temperature variations Varying signal attenuation, phase or polarization due to atmospheric humidity and/or airborne particles Varying ambient light and heat Electrical noise generated within the sensors Wavelength and/or amplitude drift in the transmitted signal, and reference wavelength drift in the receivers Any other source of signal impairment in the measurement environment.

From the foregoing, it will be appreciated that specific embodiments of the invention have been described herein for purposes of illustration, but that various modifications may be made without deviating from the spirit and scope of the various embodiments of the invention. Further, while various advantages associated with certain embodiments of the invention have been described above in the context of those embodiments, other embodiments may also exhibit such advantages, and not all embodiments need necessarily exhibit such advantages to fall within the scope of the invention. Accordingly, the invention is not limited, except as by the appended claims.

We claim:

1. A non-contacting system for measuring the dopant content of semiconductor material, comprising:
   a) an infrared radiation source configured to focus infrared radiation on a point on the material;
   b) a modulator for modulating the radiation from the source before the radiation strikes the material;
   c) a first lens is positioned to collect the radiation reflected from the material and focus the radiation;
   d) a first band pass filter positioned to receive the radiation from the first lens, the first filter configured to pass a narrow wavelength band of the radiation through the filter and reflect the balance of the radiation, the first filter passing a narrow hand of infrared radiation centered at a selected wavelength of the infrared radiation source;
   e) a second band pass filter positioned to receive the radiation that reflects off the first filter, the second filter configured to pass a narrow wavelength band of the radiation through the second filter and configured so that the narrow wavelength band that is passed by the second filter is different as compared to the narrow wavelength band passed by the first filter, the second filter passing a narrow wavelength, of infrared radiation centered at a selected wavelength of the infrared radiation source;
   f) a first radiation detector positioned to receive the radiation that passes the first band pass filter and configured to determine a first level of energy;
   g) a second radiation detector positioned to receive the radiation that passes the second filter and configured to determine a second level of energy; and
   h) a calculator configured to compare the first and second levels and return a dopant content value using a correlation curve, the correlation curve relating the dopant content of the semiconductor material based on a comparison of the level of energy reaching the two detectors for a series of the same semiconductor material of known different levels of dopant content.

2. The system of claim 1 further comprising a focusing device between the modulator and the semiconductor material to focus the radiation on the point on the material, selected from the group:
   a) a parabolic reflector;
   b) an adjustable reflector;
   c) an elliptical reflector;
   d) a parabolic lens; and
   e) an optical lens.

3. The system in claim 2 wherein the focusing device is configured to direct the radiation on the point at a 45 degree angle with respect to the surface of the material.

4. The system of claim 1 wherein the modulator is selected from the group:
   a) a modulator using high speed chopping wheel;
   b) a modulator using pulse modulation of the source; and
   c) a modulator using frequency modulation of the source.

5. The system of claim 1 wherein the semiconductor material is selected from the group:
   a) a doped silicon material;
   b) an undoped silicon material;
   c) a doped germanium material;
   d) an undoped germanium material;
   e) a doped indium material;
   f) undoped indium material;
   g) doped or undoped silicon or germanium material combined with aluminum, boron, gallium, indium phosphorus, arsenic and antimony elements; and
   h) a thin film of any of the above materials on a substrate which may be a semiconductor, or may be a non-conductive material.

6. The system of claim 1 further comprising a second lens positioned to receive the radiation that passes through the second band pass filter and configured to focus the radiation on the first detector.

7. The system of claim 6 further comprising a third lens positioned to receive the radiation which reflects from the first band pass filter and configured to focus the radiation on the second detector.

8. The system of claim 1 further comprising a third lens positioned to receive the radiation which reflects from the first band pass filter and configured to focus the radiation on the second detector.

9. The system in claim 1 wherein the radiation source is a multi-wavelength infrared laser.

10. The system in claim 1 wherein the radiation source is a source of broadband infrared radiation.

11. The system in claim 1 wherein the pass-band of each band pass filter is between 50 nanometers and 500 nanometers in width.

12. The system in claim 1 wherein the center of the pass-band for one filter is between 1 and 20 micrometers.

13. The system in claim 1 wherein the center wavelength of the pass-band for the second filter is between 1 and 20 micrometers and different than the center wavelength of the pass-band of the first filter.

14. The system in claim 1 wherein the difference between the center wavelengths of the first and second filters is between 1 and 10 micrometers.

15. The system in claim 1 wherein the difference between the center wavelengths of the first and second filters is 2 micrometers.

16. The system in claim 1 wherein the center wavelength of the first filter is set at 8.06 micrometers and the center wavelength of the second filter is set to 10.5 micrometers with each filter having a pass-band width of between 200 and 400 nanometers.

17. The system in claim 1 wherein one band pass filter has the central band-pass at approximately 8 micrometers with a pass-band of +/−125 nanometers and the other filter has the central band-pass at approximately 10.5 micrometers with a pass-band of +/−175 nanometers.

18. The system in claim 1 wherein the detectors after each filter are mass-spectrometer detectors capable of measuring the power in a user-selected narrow wavelength band.

19. The system in claim 1 wherein the source focuses the radiation at a selected focus area and wherein the modulator is a chopping wheel configured to modulate the radiation at the focus area.

20. The system of claim 1 wherein the radiation source is composed of two single-wavelength infrared lasers.

21. The system of claim 1 wherein the radiation source is a laser with a selectable wavelength, the laser being alternated between two or more wavelengths.

22. The system of claim 1 wherein the calculator is configured to compare the first and second levels by calculating the difference between the first and second levels divided by the difference between the center wavelength of each of the first and second filters.

23. The system of claim 1 wherein the calculator is configured to compare the first and second levels by calculating the ratio of the first and second levels.

24. The system of claim 1 wherein the calculator is configured to determine a slope from the first and second levels wherein different slopes represent different amounts of the dopant being detected.

25. A non-contacting system for measuring the dopant content of semiconductor material, comprising:
   a) a broadband infrared radiation source configured to focus infrared radiation on a point on the semiconductor material;
   b) a modulator for modulating the infrared radiation from the source before the radiation strikes the semiconductor material;
   c) a first lens is positioned to collect the infrared radiation reflected from the semiconductor material and focus the radiation;
   d) a beam splitter positioned adjacent the focus point of the first lens, the splitter configured to split the infrared radiation passing through the lens into first and second streams of infrared radiation;
   e) first narrow band pass filter configured to receive the first stream of infrared radiation and to pass infrared radiation from the first stream of infrared radiation that is centered at a first predetermined wavelength of the infrared radiation source;
   f) a second narrow band pass filter configured to receive the second stream of infrared radiation and to pass infrared radiation from the second stream of infrared radiation that is centered at a second predetermined wavelength of the infrared radiation, source that is different from the first predetermined wavelength;
   g) a first infrared detector positioned to receive and configured to determine the energy level of the radiation that passes through the first band pass filter;
   h) a point on the silicon; tor positioned to receive and configured to determine the energy level of the radiation that passes through the second band pass filter; and
   i) a calculator configured to compare the first and second levels and return a dopant content value by using a correlation curve, the correlation curve relating the dopant content of the semiconductor material based on a comparison of the level of energy reaching the two detectors for a series of the same semiconductor material of known different levels of dopant content.

26. A method of non-contact measurement of the dopant content of a semiconductor material, comprising the steps of:
   a) directing a modulated infrared radiation source on a measurement point on the material;
   b) directing the radiation from the material that results from the directing of the infrared radiation source on the material onto a first band pass filter, the first band pass filter configured to pass a wavelength range of the radiation that is in the wavelength range of the radiation source through the first band pass filter and reflect the balance of the radiation;
   c) directing the radiation reflected off the first band pass filter onto a second band pass filter, the second band pass filter configured to pass a wavelength range of the radiation that is in the wavelength range of the radiation source through the second band pass filter, the second band pass filter being configured so that the wavelength range passed by the second band pass filter is different as compared to the wavelength range passed by the first band pass filter;
   d) determine the level of energy of the radiation that passes the first band pass filter;
   e) determine the level of energy of the radiation that passes the second band pass filter;
   f) comparing the levels of energy determined at steps d. and e.; and
   g) based on the comparison, calculating the dopant content of the material by using a correlation curve, the correlation curve relating the dopant content of the semiconductor material based on a comparison of the level of energy reaching the two sensors for a series of the same semiconductor material of known different levels of dopant content.

27. A method of determining the impact of the one or more process steps in a semiconductor material fabrication line upon semiconductor wafers, comprising the steps of:
   a) placing a first non-contacting system for measuring the dopant content of semiconductor material at a selected upstream point of the one or more process steps of the line in position to determine the level of dopant content of wafers at the upstream point in the line, the step of placing a first system comprising placing a first system comprising;
      an infrared radiation source configured to focus infrared radiation on a point on the material;
      a modulator for modulating the radiation from the source before the radiation strikes the material;
      a lens positioned to collect and focus the infrared radiation from the material resulting from infrared radiation from the radiation source;
      a first band pass filter positioned to receive the radiation from the first lens, the first filter configured to pass a narrow wavelength band of the radiation through the filter and reflect the balance of the radiation;
      a second band pass filter positioned to receive the radiation that reflects off the first filter, the second filter configured to pass a narrow wavelength band of the radiation through the second filter and configured so that the wavelength band that is passed is different as compared to the narrow wavelength band passed by the first filter;
      a first radiation detector positioned to receive the radiation that passes the first band pass filter and configured to determine a first level of energy;
      a second radiation detector positioned to receive the radiation that passes the second filter and configured to determine a second level of energy; and
      a calculator configured to compare the first and second levels and return a dopant content value using a correlation curve, the correlation curve relating the dopant content of the semiconductor material based on a comparison of the level of energy reaching the two sensors for a series of the same semiconductor material of known different levels of dopant content;
   b) placing a second non-contacting system for measuring the dopant content of semiconductor material at a selected downstream point of the one or more process steps of the line in position to determine the level of dopant content of wafers at the downstream point in the line, the step of placing a second system comprising placing a second system comprising;
      an infrared radiation source configured to focus infrared radiation on a point on the material;
      a modulator for modulating the radiation from the source before the radiation strikes the material;
      a lens positioned to collect and focus the radiation from the material resulting from the infrared radiation from the radiation source;
      a first band pass filter positioned to receive the radiation from the first lens, the first filter configured to pass a narrow wavelength band of the radiation through the filter and reflect the balance of the radiation;

a second band pass filter positioned to receive the radiation that reflects off the first filter, the second filter configured to pass a narrow wavelength band of the radiation through the second filter and configured so that the wavelength band that is passed is different as compared to the narrow wavelength band passed by the first filter;

a first radiation detector positioned to receive the radiation that passes the first band pass filter and configured to determine a first level of energy;

a second radiation detector positioned to receive the radiation that passes the second filter and configured to determine a second level of energy; and a calculator configured to compare the first and second levels and return a dopant content value using a correlation curve, the correlation curve relating the dopant content of the semiconductor material based on a comparison of the level of energy reaching the two sensors for a series of the same semiconductor material of known different levels of dopant content;

c) operating the fabrication line to move a series of wafers from the upstream point to the downstream point through the one or more processing steps;

d) using the first system to determine the level of dopant content of wafers at the upstream point of the line;

e) using the second system to determine the level of dopant content of wafers at the downstream point of the line; and f) comparing the level of dopant content of the wafers at the downstream point to the level of dopant content at the upstream point to obtain a difference in level of dopant between the wafers at the upstream point and the wafers at the downstream point.

28. The method of claim 27, wherein the one or more processing steps are performed by one or more of, or a combination of: a wet dopant chemical application machine, a wet dopant carrier drying machine, an in-line diffusion furnace, a batch diffusion furnace, a laser annealing machine, an ion implantation machine, an epitaxial layer deposition machine, a PSG etching machine, a wafer etching machine, and a wafer texturing machine.

29. The method of claim 28 wherein the one or more processing steps are performed by a wet dopant chemical application machine.

* * * * *

UNITED STATES PATENT AND TRADEMARK OFFICE
CERTIFICATE OF CORRECTION

PATENT NO.        : 8,829,442 B2                                    Page 1 of 1
APPLICATION NO.   : 13/696056
DATED             : September 9, 2014
INVENTOR(S)       : Heaven et al.

It is certified that error appears in the above-identified patent and that said Letters Patent is hereby corrected as shown below:

In the Claims:

Claim 1, e): Column 13, line 25, "wavelength," should read -- wavelength --

Signed and Sealed this
Seventeenth Day of May, 2016

Michelle K. Lee
*Director of the United States Patent and Trademark Office*